United States Patent [19]

Fehr

[11] 4,122,177
[45] Oct. 24, 1978

[54] METHOD OF TREATING OLIGOSPERMIA AND ASTHENOSPERMIA

[75] Inventor: Hans Ulrich Fehr, Bischofszell, Switzerland

[73] Assignee: Sandoz Ltd., Basel, Switzerland

[21] Appl. No.: 829,854

[22] Filed: Sep. 1, 1977

[30] Foreign Application Priority Data

Sep. 2, 1976 [GB] United Kingdom ............ 36366/76

[51] Int. Cl.² .................. A61K 31/495; A61K 31/48
[52] U.S. Cl. ................................. 424/250; 424/261
[58] Field of Search ........................... 424/250, 261

[56] References Cited

U.S. PATENT DOCUMENTS 3,336,311  8/1967  Hofmann et al. ................. 260/268

OTHER PUBLICATIONS

Joël, Fertility Disturbances in Men & Women, Karger, New York, 1971, pp. 278-285.

*Primary Examiner*—Donald B. Moyer
*Attorney, Agent, or Firm*—Gerald D. Sharkin; Robert S. Honor; Thomas O. McGovern

[57] ABSTRACT

The present invention relates to a new use of an active agent selected from compounds of formula I, wherein
  $R_1$ is hydrogen or alkyl of 1 to 5 carbon atoms,
  $R_2$ is hydrogen, alkyl of 1 to 5 carbon atoms or benzyl, and
  $R_3$ is hydrogen or alkyl of 1 to 4 carbon atoms,
in the treatment of oligosphermia and asthenospermia.

8 Claims, No Drawings

METHOD OF TREATING OLIGOSPERMIA AND ASTHENOSPERMIA

The present invention relates to a new use of an active agent selected from compounds of formula I,

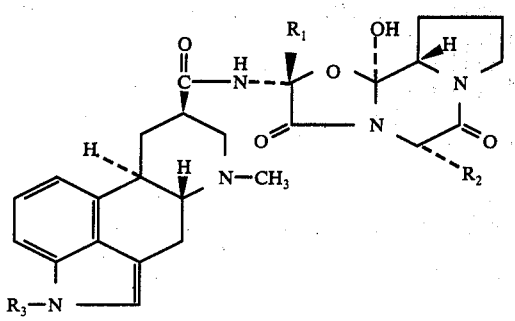

wherein
$R_1$ is hydrogen or alkyl of 1 to 5 carbon atoms,
$R_2$ is hydrogen, alkyl of 1 to 5 carbon atoms or benzyl, and
$R_3$ is hydrogen or alkyl of 1 to 4 carbon atoms, e.g. dihydroergovaline, dihydroergonine, dihydroergosine, dihydroergotamine and dihydroergotoxine and any of its components, i.e. dihydroergocornine, dihydroergocristine, β-dihydroergocryptine and α-dihydroergocryptine.

These active agents have now been found to be useful in the treatment of oligospermia and asthenospermia in male animals, as indicated clinically, e.g. in families who had not been able to produce children.

In one instance, a 40 year old man having an abnormally low sperm concentration and also having sperm of abnormally low mobility and activity, took 3 tablets daily of 1.5 mg dihydroergotoxine [HYDERGIN$^R$] each. His wife, who had been unable to conceive for over 7 years conceived within a month. Treatment was then stopped.

In a second instance, the same man who had again an abnormally low sperm concentration, mobility and activity took three tablets daily each containing 1 mg dihydroergotamine. His wife conceived within a month.

For the above-mentioned uses the dosage will, of course, vary depending on the mode of administration, therapy desired and active agent used. However, in general, satisfactory results are obtained when the active agent is administered at a daily dosage of from about 0.001 to about 0.1 mg per kg animal body weight, conveniently given in divided doses 2 to 4 times a day or in sustained release form. For the larger mammal, the total daily dosage is in the range from about 0.1 to about 10 mg (preferably 0.5 to 6 mg) of the active agent, and dosage forms suitable for oral administration comprise from about 0.025 mg to about 5 mg of the compounds admixed with a solid or liquid pharmaceutical carrier or diluent.

The active agent may be administered in free base form or in pharmaceutically acceptable acid addition salt form, e.g. the hydrochloride or mesylate.

The active agent may be administered orally in the form of tablets, powders, granules, capsules, suspensions, sirups and elixirs, or parenterally in the form of injectable solutions or suspensions. Oral administration is preferred. Aside from the active agent the preparations may contain pharmaceutically inert organic or inorganic adjuvants, optionally granulating agents, binding agents, lubricants, dispersing agents, wetting agents and preservatives. Moreover, the pharmaceutical preparations may contain colouring, flavouring and sweetening substances, etc. Adjuvants for the production of tablets may be calcium carbonate, lactose, microcrystalline cellulose, mannitol or talc. Starch and alginic acid or microcrystalline cellulose may be used as granulating and disintegrating agents, starch, polyvinylpyrrolidone and gelatine may be used as binding agents, and magnesium stearate, stearic acid and talc as lubricants. Tablet formulations may be coated. Suitable suspending agents for the production of liquid administration forms are especially methyl cellulose, tragacanth and sodium alginate. Suitable wetting agents are e.g. polyoxyethylene stearate and polyoxyethylene sorbitan-monooleate. Furthermore, preservatives such as p-hydroxy-benzoic acid alkyl ester may be used. Capsule formulations may contain the active agent on its own or together with an inert solid diluent, for example calcium phosphate, starch, lactose, mannitol, and microcrystalline cellulose.

Solid preparations are preferred, especially hard-filled capsules and tablets, for reasons of easier production and favourable administration.

The present invention also provides a pack containing a pharmaceutical preparation comprising an above-mentioned active agent in physical relation to instructions for the use of the preparation in the treatment of oligospermia and asthenospermia.

The following compositions may be used in the method of the invention:

EXAMPLE 1

Dihydroergotamine tablets

Each tablet contains:
Dihydroergotamine mesylate: 1.015 mg
Tartaric acid: 0.1 mg
Lactose (pulverized): 84.985 mg
Corn starch: 8.00 mg
Gelatine: 0.3 mg
Magnesium stearate: 0.5 mg
Stearic acid: 1.1 mg
Talc: 4 mg
and may be administered three times daily to a man suffering from oligospermia or asthenospermia.

EXAMPLE 2

Dihydroergotoxin tablets

Each tablet contains:
Dihydroergotoxin mesylate: 1.015 mg
Stearic acid: 2 mg
Polyvinylpyrrolidone: 4 mg
Talc: 4 mg
Corn starch: 8 mg
Lactose: 140.985 mg
and may be administered to a male suffering from oligospermia three times a day.

If desired tablets may be made with 0.25 mg of 1.5 mg of dihydroergotoxin mesylate in analogous manner.

I claim:
1. A method of treating a male animal suffering from oligospermia or asthenospermia which comprises administering a therapeutically effective amount of an active agent which consists of a compound or compounds of formula I,

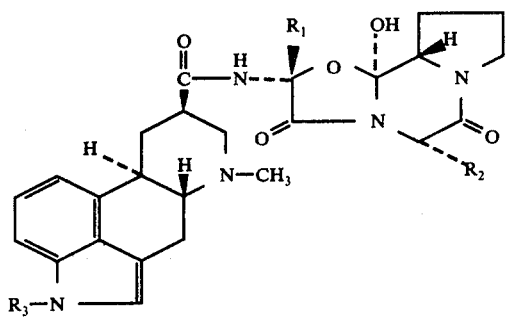

wherein
$R_1$ is hydrogen or alkyl of 1 to 5 carbon atoms,
$R_2$ is hydrogen, alkyl of 1 to 5 carbon atoms or benzyl, and
$R_3$ is hydrogen or alkyl of 1 to 4 carbon atoms,
to a male animal in need of such treatment.

2. A method of claim 1, wherein the active agent is selected from at least one of dihydroergotamine, dihydroergotoxine, dihydroergocornine, dihydroergocristine, β-dihydroergocryptine and α-dihydroergocryptine.

3. The method of claim 1, wherein the active agent is dihydroergotamine.

4. The method of claim 1, wherein the active agent is dihydroergotoxine.

5. The method of claim 1, wherein the active agent is administered at a daily dosage of from 0.001 to 0.1 mg/kg.

6. The method of claim 1, wherein the active agent is administered at a daily dosage of from 0.1 to 10 mg.

7. The method of claim 1, wherein the active agent is administered in unit dosage form containing from 0.025 to 5 mg of the active agent.

8. The method of claim 1, wherein the animal is suffering from oligospermia.

* * * * *